United States Patent [19]
Rosen et al.

[11] Patent Number: 4,816,402
[45] Date of Patent: Mar. 28, 1989

[54] MURINE HYBRIDOMA AND DIAGNOSTIC ANTIBODY PRODUCED THEREBY

[75] Inventors: Steven T. Rosen; James A. Radosevich; Yixing Ma, all of Chicago, Ill.

[73] Assignee: Northwestern University, Evanston, Ill.

[21] Appl. No.: 816,709

[22] Filed: Jan. 7, 1986

[51] Int. Cl.$^4$ .................... G01N 33/577; C12N 15/00
[52] U.S. Cl. ................... 435/240.27; 435/68; 435/172.2; 435/7; 530/387; 530/808; 530/809; 935/104; 935/110; 436/548; 436/813
[58] Field of Search .......... 435/240, 68, 172.2, 270.27, 435/7; 935/89, 102–104, 110; 530/387, 808, 809; 424/317.1; 436/548, 813

[56] References Cited
FOREIGN PATENT DOCUMENTS 154550 9/1985 European Pat. Off. ............ 435/240

OTHER PUBLICATIONS

Yarki et al., Cancer Res., 44(1984) 681–687.
Mulshine et al., J. Immunol., 131(1983) 497–502.
Yoshida et al., Chem. Abstracts 103(1985)#213228n.
Rosen et al., Cancer Res. 44(1984)2052–2061.
Mazauric et al., Cancer Res. 42(1982) 150–154.
Ho et al., Cancer, Res. 47(1987) 241–250.
Nakamura; Chem. Abstracts, 104(1986)#49618n.
S. G. Combs, et al., Expression of the Antigenic Determinant Recognized by the Monoclonal antibody 44–3A6 on Select Human Adenocarcinomas and Normal Human tissues, Manuscript (submitted for publishing).
Inchul Lee, et al., Cancer Research vol. 45, Nov. '85.
Barbara F. Banner, M.D., et al., Diag. Cytopathol, vol. 1, #4 '85.
J. A. Radosevich, et al., Cancer Research, vol. 45, Nov. '85.
Inchul Lee, et al., Amer. J. of Pathology, vol. 123, No. 3, 1986.
A. M. Zimmer, et al., Abstract for Fourth Annual Congress for Hybridoma Research, Feb. 1985.
I. Lee, et al., Abstract for American Federation for Clinical Research, Jan. 6, 1985.
I. Lee, et al., Abstract for International Academy of Pathology.
S. G. Combs, et al., Abstract for International Academy of Pathology.
B. F. Banner, et al., Abstract for International Academy of Pathology.
B. F. Banner, et al., Abstract for 33rd Annual Meeting of the American Society of Cytology.
S. G. Combs, et al., Abstract for Midwest Section, American Federation of Clinical Research.
J. A. Radosevich, et al., Abstract for IV World Conference on Lung Cancer, Aug. 25–30, 1985, Toronto, Canada.
I. Lee, et al., Abstract for IV World Conference on Lung Cancer, Aug. 25–30, 1985, Toronto, Canada.
A. M. Zimmer, et al., Central Chapter, Society of Nuclear Medicine, Inc.

Primary Examiner—Christine M. Nucker
Attorney, Agent, or Firm—Tilton, Fallon, Lungmus & Chestnut

[57] ABSTRACT

Hybridoma HB 8986 produces a murine monoclonal antibody which recognizes a new determinant expressed in bronchopulmonary carcinomas and A549 cell line derived tumors. Immunoperoxidase staining with the hybridoma on formalin fixed, paraffin embedded tissues shows that it specifically stains both the cytoplasmic and cell surface. The monoclonal antibody has the ability to distinguish preferably bronchopulmonary carcinomas with glandular differentiation from other bronchopulmonary carcinomas. Additionally, the monoclonal antibody may identify adenocarcinomas through the body.

2 Claims, No Drawings

MURINE HYBRIDOMA AND DIAGNOSTIC ANTIBODY PRODUCED THEREBY

This invention was made in the course of research supported by the Veterans Administration (Merit Review Award Number 005-114-42-5054).

FIELD OF INVENTION

The field of this invention is hybridomas and monoclonal antibodies. More specifically, this invention relates to hybridoma produced monoclonal antibody which identifies adenocarcinoma surface antigens, and which is useful in the diagnosis of bronchopulmonary and non-pulmonary carcinomas.

BACKGROUND AND PRIOR ART

The fusion of myeloma cells to spleen cells from immunized mice by Kohler and Milstein in 1975 [Nature 256 495-597 (1975)] demonstrated for the first time that it was possible to obtain a continuous cell line making homogenous (so called "monoclonal") antibodies. Since this seminal work, much effort has been directed to the production of various hybrid cells (called "hybridomas") and to the use of the antibody made by these hybridomas for various scientific investigations.

The general method of production of hybrid cell lines of the type described above comprises the steps of immunizing a animal (usually a rat or mouse, but not necessarily one of these) with an antigen to which a monoclonal antibody is required. After allowing time for the immune system to generate lymphocytes secreting the antibodies to the antigen, the animal is sacrificed and a suspension of spleen cells is prepared. Fusion between these cells and myeloma cells is achieved by bringing them into contact in the presence of a fusion promoter (e.g. polyethylene glycol). A small percentage of the cells fuse to produce hybrid myeloma cells. The immunization results in a plurality of different lymphocytes each secreting antibody to a different antigenic determinant, and these characteristics are transferred genetically to the hybrid cells. It is possible, by careful screening, to isolate from a culture of hybrid cells, a cell having the desired specificity. Such cells may be cloned and cultured.

The advantage of this technique is that it provides a source of a specific antibody uncontaminated by antibodies raised to other determinants either on the antigen with which the mammal was immunized or on antigenic impurities in the immunizing material. Another advantage of the technique is that antigen not available in a pure form for screening assays and present in the immunizing material at low concentrations, may be used.

The present invention concerns a monoclonal antibody to bronchopulmonary carcinomas that may classify various bronchopulmonary carcinomas and identify one specific lung carcinoma type, adenocarcinoma, while additionally identifying adenocarcinoma in non-pulmonary sites.

The increasing clinical and epidemiologic significance of bronchopulmonary carcinomas is a matter of serious concern. Pathologically, bronchopulmonary neoplasms encompass several types: squamous cell carcinoma (SCC), adenocarcinoma (AC), adenosquamous carcinoma (ASC), large cell carcinoma (LCC), bronchioloalveolar carcinoma (BAC), small cell neuroendocrine carcinoma (SCNC), intermediate cell neuroendocrine carcinoma (ICNC), well-differentiated neuroendocrine carcinoma (WDNC), carcinoid, and other rare entities such as mucoepidermoid carcinoma, adenoid cystic carcinoma and carcinosarcoma.

The classification of bronchopulmonary neoplasms on the basis of conventional morphology is difficult, because the pattern of differentiation of individual neoplasms may vary markedly; and, the diagnostic criteria may vary considerably among pathologists. Moreover, one may see carcinomas with various admixtures of SCC, AC, and neuroendocrine (NE) carcinoma differentiation, etc. There are also "poorly" "differentiating carcinomas", which by conventional light microscopy do not express a definite pattern of differentiation; these are usually classified at LCC's. For purposes of this invention, bronchopulmonary refers to the bronchial tubes, pulmonary system and lungs.

The terminology used in identifying carcinomas is often difficult to interpret because of the rapidly changing art being developed to classify carcinomas. As more characteristics of carcinomas are discovered, they may be re-classified into different groups.

It would be most helpful to pathologists to have monoclonal antibodies available for the classification of the different types of bronchopulmonary carcinomas and one that would specifically identify adenocarcinoma. Additionally, it would be helpful to pathologists if the monoclonal antibody will be reactive in fixed paraffin embedded tissues. Many antibody preparations are only useful in flow cytometric analysis, with frozen section, and in radial immuno- and ELISA assays. It is more convenient to use standard immunohistochemical techniques to study the phenotypic characteristics of tissues and tumors. In particular, there is a recognized need for monoclonal antibodies which may classify bronchopulmonary carcinomas and specifically identify bronchocarcinomas and adenocarcinomas throughout the body and which may be used with fixed paraffin embedded tissues.

Several investigators have attempted to produce monoclonal antibodies that will distinguish the various types of lung carcinomas. Brenner et al. (Brenner B. G., Jothy S., and Shuster J. Monoclonal Antibodies to Human Lung Tumor Antigens Demonstrative by Immunofluorescence and Immunoprecipitation Cancer Research 42:3187-3192 (1982) describe the production of monoclonal antibodies directed against glycoprotein antigens with molecular weights of 25,000 KD and 11,500 KD that had been purified from a squamous cell lung cancer extract by anti-$B_2$-microglobulin affinity chromatography. Varki et al. (Varki N. M., Reisfield R. A., Walker L. E. Antigens Associated with Human Lung Adenocarcinoma defined by Monoclonal Antibodies. Cancer Research 44:681-687, (1984) discuss three monoclonal antibodies raised against UCLA $P_3$, an adenocarcinoma of the lung cell line; K S ¼ and K S 1/17 recognizing different epitopes of glycoprotein with a molecular weight of 40,000 KD and KS 1/9, recognizing a presumed glycolipid. With these antibodies, cross reactivity was seen with all types of lung carcinomas. Mazauric et al. (Mazauric T., Mitchell K. F., Letchworth G. J. III, et al. Monoclonal Antibody-Defined Human Lung Cell Surface Protein Antigen. Cancer Research 42:150-154 (1982) produced four monoclonal reagents against a variety of human lung carcinoma cell lines whose provenance was not clearly detailed. The antibodies reacted with glycoproteins with a molecular weight of 37,000 and 19,000; 127,000; 126,000; 149,000; and 119,000. A limited number of tumor cell lines were tested to establish their binding profile. Brown, et al. (Brown D. T. and Moore M.) Monoclonal Antibodies Against Two Human Lung Carcinoma Cell Lines. Br. J. Cancer 46:794–801, (1982) isolated two monoclonal antibodies recognizing antigens present in squamous cell lung carcinoma. The antigens were quantatively abundant in squamous cell carcinomas but were not restricted to this tumor type. Identification of the target antigens was not accomplished. Mulshine et al. (Mulshine J. et al., Cuttitta F., Bibro M., et al.) Monoclonal Antibodies that Distinguish Non-Small Cell Lung Cancer from Small Cell Lung Cancer. *J. Immuno* 131:497–502, (1983) have reported two monoclonal antibodies directed against different epitopes of a 31,000 KD protein present in the cytoplasm of large cell lung carcinoma. These antibodies bound to 11/13 non-SCLC cell lines and 0/11 SCLC cell lines. The antigen was present in several non-lung cancer tumors. In addition, Rosen et al. (Rosen S. T., Mulshine J. L., Kuti F., et al.) Analysis of Human Small Cell Lung Cancer Differentiation Antigens Using a Panel of Rat Monoclonal Antibodies. *Cancer Research* 44:2052–2061, (1984) have poduced a panel of rat IgM monoclonal antibodies that recognize glycolipid antigens associated with several types of pulmonary carcinomas.

SUMMARY OF THE INVENTION

Cultures of the hybridoma (designated 44-3A6) of this invention have been placed on deposit with the American Type Culture Collection, Rockville, Md. The hybridoma has been assigned the ATCC Accession No. HB 8986.

The hybridoma clone, HB 8986, was produced from the fusion of primed mouse splenocytes and mouse myeloma cells. Hybridoma HB 8986, produces a murine IgG$_1$ monoclonal antibody which recognizes an antigen on the cell surface of adenocarcinoma of the lung and on non-pulmonary sites. Immunoperoxidase staining with HB 8986 on formalin fixed, paraffin embedded tissues shows that it specifically stains both the cytoplasmic and cell surface. The antibody produced from HB 8986 generally reacts with and causes the staining of subset of neoplasms presently known as adenocarcinomas. Certain human adenocarcinomas including pulmonary adenocarcinoma react with the monoclonal antibody. The monoclonal antibody has the ability to distinguish lung carcinomas with glandular differentiation from other lung carcinomas lacking these features, and it may be useful as both a diagnostic and therapeutic agent. Adenocarcinomas of the stomach, colon, pancreas, gall bladder and breast also react with the monoclonal antibody.

DETAILED DESCRIPTION

The antigenic preparation used in obtaining the hybridoma HB 8986 consisted of the well characterized human adenocarcinoma cell line, A549 available from the American National Cancer Institute Culture Collection, Rockville, Md. Briefly, the hybridoma clone HB 8986 was produced by the fusion of mouse myeloma cell line SP2/0.Ag14 and Balb/c splenocytes obtained from a mouse hyperimmunized with the human adenocarcinoma cell line, A549. Polyethylene glycol was used as the fusion agent. Only one hybrid line was derived from any one of the original 480 wells used in plating the hybrids after the fusion. The hybridoma producing monoclonal antibody was selected after initial screening and was subsequently cloned three times in soft agar.

Ascites fluid was prepared by intraperitoneal implantation of $1 \times 10^7$ hybridoma cells in the Balb/c mice which have been pristane-primed three to seven days prior to injection. The monoclonal antibody was purified by 50% ammonium sulfate precipitation followed by affinity chromotography using Staphylococcus Protein-A. Protein concentrations were determined using the Bio-Rad protein assay kit using bovine plasma gamma globulin as a standard. Supernatants, ascites fluids, and purified antibodies samples were stored with a final concentration of 0.02% sodium azide or sterile filtered, at either 4° C. or minus 70° C.

The monoclonal antibody produced by the hybridoma HB 8986 was tested to determine its properties and specificity of the HB 8986 antibody molecules. These tests and results are described below. The primary morphological characteristics of hybridoma HB 8986 are as follows:

1. Origin: It was produced by fusion of SP2/0.Ag14 mouse myeloma cells with Balb/c mouse splenocytes primed with human adenocarcinoma cell line A549.
2. Cultivation: The hybridoma grows in 10% Fetal Calf Serum/90% RPMI-1640 at 37° C., with 5% $CO_2$/95% air. The hybrid can be adapted to a variety of other media and growth conditions. Frozen storage of the cell line may be in either 10% Dimethylsulfoxide or 10% glycerine.
3. Properties: The HB 8986 hybridoma is not phytopathogenic and has not known to have any dangerous properties. It is tumorigenic in Balb/c mice.
4. Antibody: The HB 8986 hybridoma produces a murine IgG$_1$ monoclonal antibody which stains the cytoplasm and cell surface of some fixed tissue (i.e. formalin) paraffin embedded human lung adenocarcinomas.
5. Testing: The production of HB 8986 antibody by the hybridoma cells can be tested by the Avidin Biotin Complex Method or by a variety of other methods on formalin fixed paraffin embedded human bronchopulmonary carcinomas, or on cell lines. Alternatively RIA methods may be used.

The HB 8986 hybridoma may be propagated in vitro at an initial cell concentration of one cell per flask. The cells are grown in stationary suspension culture up to $3 \times 10^6$ cells/ml.

Using the culturing procedure described above, the HB 8986 antibody may also be produced. The antibody is obtained by centrifuging to remove the cells, and saving the supernatant.

To obtain larger yields of higher concentrations of HB 8986 antibody, the hybridoma may be injected into the peritoneal cavity of pristane primed Balb/c mice. The injected hybridoma will cause formation of ascites in the peritoneal cavity, which will result in fluid containing a high concentration of the desired antibody.

Literature references describing the foregoing procedures are: *Monoclonal Antibodies Hybridomas: A New New Dimension in Biological Analysis.* R. H. Kennett, T. J. McKeam, and K. B. Bechtol. Plenum Press, New York, 1980.

EXPERIMENTAL

The Scientific basis of the present invention will be more fully understood from the following description of the research investigations which led to the invention.

MATERIALS AND METHODS

1. Antigen preparation: The human lung carcinoma cell line A549 was harvested at mid-log growth phase using a rubber policeman to dislodge the cells from the flask. The cell suspension was triturated gently and washed three times with PBS. The cells were then resuspended in 0.5 ml of PBS and an emulsion of Freund's complete or incomplete adjuvant was prepared by sonication.
2. Immunization protocol: The mouse was injected on day 1 with 1 ml of emulsion using Freund's complete adjuvant emulsion. Days 7, 14 and 21 with 1 ml of Freund's complete adjuvant emulsion. The mouse was then rested for four weeks and boosted 3 days prior to fusion with Freund's incomplete adjuvant emulsion.
3. Serologic characterization: Prior to splenectomy, a small sample of serum was obtained from the mouse, and tested by radioimmunoassay (as described below) for the presences of antibodies reacting with the human lung carcinoma cell line, A549.
4. Splenocyte preparation: On the day of the fusion, a splenectomy was preformed on the mouse. The spleen was then teased under sterile conditions in RPMI-1640.
5. Cell fusion: Washed splenocytes and SP 2/0.Ag14 were combined at a ratio of 2:1. One ml of 50% PEG was added dropwise to the cells over a 60 second period. After an additional 60 seconds, 5 mls of RPMI-1640 was used to dilute the cells slowly. An additional 10 mls of RPMI-1640 was then added slowly over a ten minute period.
6. Cloning: Cells which yielded positive antigen binding supernatants were selected to be clone on soft agar. The cells from each individual cell expanded and 100 $\mu$l aliquots containing $10^2$–$10^3$ cells were spread over the surface of a 13 mm soft agar plate. After 3–7 days, individual colonies were picked, grown, and tested by RIA. Each time the most positive clone was chosen. The process was repeated a total of three times.

Radioimmunoassays

Human lung carcinoma cell line lysates were made by traditional methods. Supernatants, ascites fluid, or purified antibody (50 $\mu$l of each) was incubated at room temperature for one hour in 96 well polyvinyl chloride target plates of each cell line tested. After being washed seven times with 250 ul volumes of phosphate buffered saline (PBS), the target plates were incubated with $5 \times 10^4$ cpm of $^{125}$I-sheep-anti-mouse F(ab')$_2$ fragments in a 50 $\mu$l volume. The plates were washed seven times as stated above after a one hour incubation, and counted in a gamma counter for one minute. Controls included (when appropriate), no primary antibody, SP 2/0.Ag14 supernatant, normal mouse serum, and a monoclonal antibody at the same concentration and identical isotype. Binding ratios were calculated as reported in *Cancer Research* 44:2052–2061 (1984).

Live Cell Radioimmunoassay

Human lung carcinoma cell lines were harvested at mid-log growth phase using a rubber policeman to dislodge cell lines which adhere to the flasks. Cell suspensions were triturated gently and washed three times with PBS. $1 \times 10^5$ cells were resuspended in 100 $\mu$l of PBS containing 0.02% sodium azide and plated into microtiter wells. The microtiter plates had been pretreated for 24 hours with 1 mg/ml BSA in PBS with azide. Fifty ul of supernatant or ascites fluid (diluted 1:100) was added to each well. Plates were incubated at room temperature for thirty minutes on a platform shaker set at low speed. After the incubation period, the cells were washed seven times with cold PBS containing azide by centrifuging the plates at 1,000 rpm for 5 minutes, aspirating the supernatants, and resuspending the cells in 200 ul of PBS. $^{125}$I-sheep-anti-mouse antibody F(ab')$_2$ (50,000 cpm/50 ul) was added to each well after being washed and incubated as before. Each well was again washed seven times as before, and the wells counted in a gamma counter for one minute intervals.

Immunofluorescence

Cell lines were harvested and washed as described above. $1 \times 10^5$ cells per well were spotted onto ten well microscope slides and allowed to adhere for five minutes, and air-dried. The slides were either fixed for 12 minutes in 1% glutaraldehyde or in acetone at 0° C. Slides were stored in PBS at 4° C. until used. Each well was incubated with 100 $\mu$l of supernatant for one hour in a humidified 37° C. chamber. After three washes with PBS, the slides were incubated with fluorescein isothiocynate (FITC) labeled goat anti-mouse antibodies (Cappel, Malvern, PA), washed three times and viewed with a fluorescent microscope. Samples were scored on a scale of zero to plus four using a double blinded reviewer.

Immunoperoxidase Staining of Nude Mouse Xenografts

Nude mouse xenografts of human lung adenocarcinoma cancer cell lines A549, SKLU-1 available from the American Type Culture Collection, Rockville, Md. 20852 and human small cell lung carcinoma cell lines NCI-H69 and NCI-H60 available from the National Cancer Institute were fixed in 10% formalin and paraffin embedded using traditional methods. Material was excluded if autolysis was noted. Simultaneous analysis of an identical hematoxylin and eosin stained tissue section was performed. All tissue sections were 7 $\mu$m thick and were prepared as in a traditional method with the primary antibody being the monoclonal antibody culture supernatants. Immunoperioxidase staining using the Avidin-Biotin-Horseradish peroxidase complex method (Vector Laboratories, Burlingame, Calif.) was used as suggested by the manufacturer, and counterstained with hematoxalin. Positive tissue was tested with each set of slides and controls included no primary antibody or an antibody of the same isotype but different binding characteristics.

Results

The monoclonal antibody of this invention was produced by hyperimmining a Balb/c mouse with a human adenocarcinoma (AC) cell line A549. A stable hybridoma was obtained using SP2/0.Ag14 as a fusion partner. The monoclonal antibody is an IgG$_1$ isotype and binds Staphylococcus protein A. Using a solid phase radioimmunoassay (RIA) this antibody reacted with several human lung adinocarcinoma cell lines, but not with several human small cell lung cancer (SCLC) cell lines. Live cell RIA, immunofluorescent studies and radioimmunodetection of nude mouse AC xenografts indicate that the antigen recognized by the monoclonal antibody is on the cell surface. The antigen is preserved after formalin fixation and paraffin embedding as shown by the immunoperoxidase staining. Human AC biopsy specimens react with the monoclonal antibody, while human SCLC biopsy specimens do not react.

Screening for Selectivity of Antibody Binding

Ouchterlony analysis of twenty-five fold concentrated supernatant revealed that the antibody had an $IgG_1$ isotype. The antibody also bound to Staphylococcus Protein A, further indicating that it belonged to an IgG subclass. Stability of this clone has been demonstrated by repeated cloning on soft agar and continuous growth for months in culture with high titer antibody production. Initial screening using ten human lung cell lines showed binding to adenocarcinoma cell lines and not to eight other lung cancer cell lines representing a variety of histological types. Table 1 shows both the cpm and binding ratios (total cpm/control cpm) to the original panel of human lung lines used to screen monoclonal antibody of this invention.

TABLE 1

RIA REACTIVITY OF MCA AGAINST HUMAN LUNG CARCINOMA CELL LINES

|  | C.P.M. | BINDING RATIO |
|---|---|---|
| LYSTATE TARGET | | |
| AC LINES | | |
| H234 | 294 | 2.9 |
| 125 | 206 | 2.0 |
| SKLU-1 | 1170 | 10.0 |
| A549 | 2060 | 11.6 |
| EPIDERMOID LINE | | |
| A427 | 272 | 4.3 |
| SCLC LINES | | |
| 60 | 138 | 1.6 |
| 128 | 193 | 1.6 |
| 250 | 304 | 1.1 |
| 464 | 305 | 1.1 |
| 69 | 160 | 2.0 |
| LIVE CELL TARGET | | |
| ADENO LINES | | |
| A549 | 1602 | 3.1 |
| 125 | 1074 | 2.2 |
| SCLC LINES | | |
| 69 | 166 | 1.2 |

Live Cell Assays for Binding to Lung Cancer Cell Lines

Live cell radioimmunoassay data is shown in Table 1 as both total cpm and binding ratios. To confirm that the antibody was binding to a cell surface component, it was tested on both live and fixed human lung cancer cell lines using immunofluorescences. The adenocarcinoma line, A549 revealed cell surface binding where the remaining cell lines tested were all negative.

Immunoperoxidase Staining of Nude Mouse Xenografts

Xenograft tumor tissue of the human lung cancer cell line A549 was positive. Staining was both cytoplasmic and cell surface. While xenograft tumor tissue of human lung cancer cell line NCI-H60 did not stain, similar results were found with other small cell and adenocarcinoma cell line xenografts.

Another study was undertaken to determine if monoclonal antibody would be similarly applicable on cytologic preparations. Cytologic preparation, including bronchial brushings or fine needle aspirates, may be the earliest, or only, diagnostic material available at the time therapeutic decisions are made. The overall diagnostic accuracy for detecting malignancy in bronchial brushings 89.6% for central and 70.9% peripheral lesions as referenced in Cytology of the Lung, Techniques and Interpretation, New York, IgakuShoin, 1983, pp. 25, 29, 75-131, but the accuracy in assigning histologic types is lower, especially for a large cell undifferentiated carcinoma. The bronchial pulmonary carcinomas studied are classified into four major types:

Squamous Cell (SCC): Adenocarcinoma (AC), Large Cell Undifferentiated (LCUC) and Neuroendocrine Carcinoma (NEC).

MATERIALS AND METHODS

Thirty-Five cases of bronchial pulmonary carcinoma which had both positive bronchial brushings and tissue specimens were obtained from Rush-Presbyterian-St. Luke's Medical Center, Chicago, Ill. There was a requirement that definite diagnosis and classification of a tumor could be made on the tissue specimen, and that ample cells be present in both types of specimens for the application and unambiguous interpretation of the immunohistochemical findings. Tumors are classified as AC, LCUC, NEC, and SCC. Histological classification was based on the World Health Organization System and modified to include neuroendocrine carcinomas as described in Lab. Invest. 1983 49:519–537. Cytologic classification was made according to traditional methods as described in Cytology of the Lung: Techniques and Interpretation, New York, Igaku-Shoin, 1983 pp. 25,29,75-131.

Tissue specimens were formalin fixed paraffin embedded, and stained with HE for light microscopy. Immunohistochemistry was performed on deparaffinized sections cut from the same blocks. Cytologic specimens consisted of direct smears of brushings made at the time of bronchoscopy; these were fixed immediately in 95% alcohol and stained by the Papanicalou technique. Two slides with numerous well preserved tumor cells distributed both singlely and in clusters were selected from each case. Immunohistochemistry was performed directly on one slide, the other was destained first by passing it through graded alcohols. Immunostaining was performed with the Avidin-biotin complex method (Victor Laboratories Burlingame, Calif.). The monoclonal antibody was used at a concentration of approximately 1 ug/ml. Slides were slightly counterstained with hematoxylin for 1.5 minutes, hydrated and mounted conventionally. Negative controls were performed by omitting primary antibody and substituting a nonreactive monoclonal antibody of the same isotype.

Adenocarcinoma

Tissue specimens consisted of 6 biopsies, 5 resections, and one biopsy of a chest wall metastasis. One patient had received radiation therapy prior to both brushings and resection. Microscopically the tumors, as defined, exhibited gland formation in over 50% of the sample. Cells were of intermediate or large size, with vesicular nuclei and prominent eosinophilic nucleoli. The radiated case showed extensive necrosis and marked stromal fibrosis. Immunohistochemical staining was strongly and diffusely positive in ten cases. In two cases, tumor cells showed variably intense positivity, with some cells exhibiting only faint staining. One of these was the radiated case, and the other was a bronchioloalveolar carcinoma. In one additional case, a few foci of squamous differentiation were notably negative.

Cytologically, the brushings from seven cases had been diagnosed as "adenocarcinoma"; four were called "poorly differentiated carcinoma with features of adenocarcinoma", and one case was diagnosed as "large cell undifferentiated carcinoma with features of adenocarcinoma". Tumor cells in the brushings were distributed singly and in clusters. Nuclei ranged from 8 to 14 $\mu$m in greatest dimension and were round or oval with only mild pleomorphism. Nuclear membranes were thick. Eosinophilic nucleoli were prominent; perinucleolar parachromatin clearing was frequently seen. Cytoplasm was abundant and delicately structured; vacuoles were frequent. Occasional mitoses were present in cell clusters.

In the immunohistochemical preparations of the brushings, tumor cell clusters were easier to identify than single cells and more reliable to evaluate for positivity due to better preservation of the cytoplasm within the clusters. In ten of the twelve cases, including the radiated one, all tumor cells were strongly positive. The remaining two cases showed mostly positive and occasional negative clusters.

Large Cell Undifferentiated Carcinoma

Tissue specimens included 5 biopsies and 2 lobectomies; one of the latter was performed after radiation therapy. Microscopically, the tumors consisted of nests and sheets of large cells with marked nuclear pleomorphism, prominent eosinophilic nucleoli, and abundant eosinophilic cytoplasm. Mitoses were frequent. The previously radiated tumor displayed extensive necrosis. Four cases exhibited focal formation of gland lumens while two were felt to have some squamous features.

Immunostaining was strong and diffuse in two cases, and focal in two cases; three cases did not immunostain. The negative cases included one with features of adenocarcinoma.

Cytologically, 5 cases had been diagnosed as "large cell undifferentiated carcinoma", and two as "adenocarcinoma". All contained tumor cells distributed both singly and in clusters. Nuclei were 9 to 21 $\mu$m in greatest dimension and contained prominent, often large or irregular eosinophilic nucleoli and coarse chromatin. Cytoplasm was abundant; it ranged from delicate and vacuolated to optically dense.

Immunohistochemical staining was strongly and diffusely positive in 5 cases, variable in one case, and negative in 1 case. The negative case also had negative histology, but showed questionable features of adenocarcinoma both cytologically and histologically.

There were 3 cases with discrepancies in staining between cytology and tissue specimens. In two cases cytology was positive and tissue was negative; in the third, the radiated patient, cytology was strongly positive and tissue was weakly positive.

Neuroendocrine Carcinoma

Tissue specimens included 7 biopsies and one lobectomy. Six cases were diagnosed as neuroendocrine carcinoma, small cell type, and two as intermediate cell type. The latter pair included the case with lobectomy, which was performed for the initial-incorrect- diagnosis of adenocarcinoma. The diagnosis was subsequently revised after examination of more abundant tissue from the lobectomy; electron microscopic study of this case showed prominent membrane bound granules. The small cell carcinomas were present as sheets of cells underneath the bronchial mucosa. Necrosis and crushing artifact were prominent. Preserved nuclei were round, oval or fusiform. Nuclear molding, sparse cytoplasm and inconspicuous nucleoli were distinctive features. The intermediate cell NE carcinomas consisted of larger cells whose pleomorphic nuclei had more stippled chromatin and a more distinct cytoplasmic rim.

Immunohistochemical staining was negative in all but the resected case of intermediate cell neuroendocrine carcinoma, where a few cells were positive.

Cytologically, all of these cases had been originally diagnosed as "small cell carcinoma" except the resected case which had been diagnosed as "adenocarcinoma". Tumor cells were dispersed singly and in loosely cohesive groups in mucous strands. Small cell nuclei ranged from 5 to 10 $\mu$m. All small cell cases showed round or fusiform nuclei, stippled chromatin, absent nucleoli, and prominent nuclear molding. Necrosis was prominent. The intermediate cell cases differed by having larger nuclei, 8–13 $\mu$m in diameter, a looser chromatin pattern, identifiable though no prominent nucleoli, and considerably more cytoplasm. Cytologically, intermediate cell NE carcinomas resembled adenocarcinomas; indeed, the one case had been originally diagnosed as such.

None of these cases immunostained with the monoclonal antibody except for the case originally called adenocarcinoma, where there were occasional positive cells, as was the case in the corresponding surgical specimen.

Squamous Carcinoma

Tissue specimens consisted of 6 biopsies and two resections. The tumor was well differentiated in 1 case, moderately differentiated in 6 cases, and poorly differentiated in one case.

Immunohistochemical staining was negative in five cases; in three cases there was faint positivity around the edges of clusters, often where cells were markedly fragmented. None of these cases was convincingly positive.

Cytologically, neoplastic cells were present singly or in irregular groups. There was cellular and nuclear pleomorphism. Nuclei were hyperchromatic or vesicular, with coarse chromatin and eosinophilic nucleoli. They ranged in diameter from 9–19 $\mu$mm. Cytoplasm was plentiful, optically dense, and either eosinophilic or cyanophilic. There was scattered necrotic debris. These tumors had been diagnosed as well (2), moderately (3) or poorly (2) differentiated based on the number of keratinized cells and the degree of cellular and nuclear pleomorphism. One case had been called "large cell undifferentiated carcinoma".

Immunocytochemistry was negative in 6 cases. Faint positivity was found in occasional cells in two cases, one of which had been faintly positive in the tissue sample.

Results

Accuracy in correlating cytologic and histologic typing of bronchopulmonary tumors ranges from 75 to 94% for SCC, 68–86% for AC, 42 to 91% for LCUC and 83 to 96% for small cell NEC, According to *Cytology of the Lung Techniques and Interpretation*, New York, Igaku-Shoin, 1983, pp. 25, 29, 75–131; *Am. J. Phthol.* 1976 84:372–424; and *ACTA Cyto* 1981 25:499–505. In the foregoing study, cytology-histology correlation was 100% for AC, with the caveats that in four cases cytology samples were diagnosed as: "poorly differentiated carcinoma with features of adenocarcinoma" and one case was diagnosed as "large cell undifferentiated carcinoma with features of adenocarcinoma". Correlation for LCUC was 75% accurate; two cases were called "adenocarcinoma" on brushings. Correlation for NEC was 88% accurate; one case of intermediate cell NEC was called "adenocarcinoma" on brushings while the other was called "small cell NEC". Accuracy and correlation for SCC was 88%; one case had been diagnosed as "large cell undifferentiated carcinoma" on brushings.

The following example indicates that the monoclonal antibody of the present invention recognizes an antigen as a broad distribution and expression pattern. Immunoreactivity was found in adenocarcinomas of the gastial intestinal tract, although only a subset of the tumors showed positive staining. It is believed that this subpopulation may represent more agressive tumors since many of the tumors which showed reactivity did so in areas which were less differentiated and lacked a distinct glandular pattern. Outside the gastrointestinal tract, breast adenocarcinomas showed the most consistant staining pattern. However, overall the normal adult distribution of the antigen recognized by the monoclonal antibody is limited. The monoclonal antibody may be useful in immunotherapy, radioimmunotherapy and radioimmuno detection.

In this work, strong diffuse staining of cells in adenocarcinomas are the stomach, colon, pancreas, gall gladder and breast was noted. Adenocarcinomas arising in the endometrium, ovary, kidney, prostate, thyroid and liver were either negative or showed very vocal reactivity. Strong staining was noted in adenocarcinomas which had an undifferentiated infiltrating component. Immunoreactivity was noted in epithelial cells from the normal bronchial tract, stomach, small intestine, pancreas and colon, wherein cells from the endometrium, kidney, ovary, prostate and thyroid were negative. The monoclonal antibody of the present invention is a useful immunodiagnostic probe capable of distinguishing among a number of normal as well as transformed glandular epithelia.

METHODS AND MATERIALS

Hematoxylin and Eosin stained tissue sections were examined for the selection of tumors, normal and fetal tissue from the files of Northwestern Memorial Hospital, University of Illinois Hospital, MacNeal Memorial Hospital, and Rush Presbyterian St-Luke's Medical Center, Chicago, Ill. The neoplasms selected for the study (the number of cases used in parentheses) whereas follows: adenocarcinomas of the breast (22); stomach (20); colon-rectum (25); small bowel (2); gallbladder (4); endometrium (12); ovary (8); pancreas (2); and prostate (10); islet cell neoplasms (6); renal cell carcinoma (8); adrenal cortical carcinoma (2); pheochromocytoma (2). Material was also submitted from the City of Hope National Medical Center and consisted of breast carcinomas (71) and thirty adenocarcinomas from sites other than the lung.

Autopsy tissues were studied (four cases) to determine the normal adult distribution of the antigen. Only cases less than six hours postmortem were used in order to reduce the autolysis and to insure antigen preservation. Tissue studies included brain, trachea, lung, heart, esophagus, stomach, duodenum, jejunum, ileum, colon, pancreas, liver, adrenal gland, kidney, prostate, bladder, ovary, uterus, cervix, testes, thyroid, aorta, bone marrow, and skin. Twenty five human fetuses were similarly studied including gestational ages of 9, 18, 20, 22, 24, 28, 30, 32, 36, 38 weeks. Cases with autolysis were discarded.

All normal and neoplastic sections were fixed in 10% buffered formalin and embedded in paraffin. Immunoperoxidase staining was performed on 6 μm tissue sections. Following conventional deparaffinization, 6 μm-thick tissue sections were stained by the avidin biotin complex (ABC) technique (Vector Laboratories, Burlingame, Calif.). The monoclonal antibody was used on a concentration of 1 μg/ml. Sections were subsequently counterstained in hematoxylin for 2 minutes. Negative controls were performed by omission of the primary antibody and substituting the monoclonal antibody with an non-immune serum. Sections submitted by the City of Hope were stained in a slightly different manner as reported in *Cancer* 55:1679-1685. All immunostained tissue sections were scored for immunoreactivity on a scale of zero to 4+.

RESULTS

Normal fetal tissues were largely negative. The only consistent weak to 1+ immunostaining was seen in bladder and renal pelvis transitional cell epithelium starting at 18 weeks gestation. The staining continued consistently through week 38 of gestation save for nonreactivity noted at 24 weeks.

Immunostaining in adult normal tissues was consistently restricted to several sites predominantly within the gastrointestinal system, see Table 2.

TABLE 2

| NORMAL TISSUE DISTRIBUTION OF HB 8986 |
| --- |
| Pancreatic Islet Cells |
| Gastric Chief and Parietal Cells |
| Testicular Interstitial Cells |
| Sebaceous Glands |
| Transitional Cell Epithelium of Bladder and Renal Pelvis |
| Pulmonary Macrophages |
| Peritracheal Mucous Glands |
| Brunners Glands |
| Colonic Entercytes and Goblet Cells |
| Endocrine Glands |
| Lung |
| Breast |
| GI tract |
| Gonads |
| Kidney |
| Liver |
| Prostate |
| Uterus |

Strong staining was seen in the islet cells of the pancreas, especially along the periphery of the islets. The gastric mucosa and particularly its chief and parietal cells showed strong immunostaining. Sebaceous glands also showed strong reactivity. Staining (2+/3+) was seen in the renal pelvis and bladder transitional epithelium and in the interstitial cells of the testes. All staining appeared cytoplasmic, however, membrane staining was prominent in the transitional cells of the renal pelvis. Bronchial epithelium showed strong focal immunoreactivity but not in every case. Focal staining of endocrine cells in the small bowel was also noted. Mild staining (1+/2+) was noted in a few subtracheal mucous glands, Brunners glands, enterocytes and focal goblet cells of the colon and focal adrenal cortical cells. The only connective tissue cells which showed reactivity were adipocytes and smooth muscle cell in the gastrointestinal tract and uterus.

Adenocarcinomas of the stomach, pancreas and gall bladder showed strong cytoplasmic and/or membrane staining in a subset of tumors as noted in Table 3.

TABLE 3

| ADENOCARCINOMA DISTRIBUTION OF HB-8986 | | |
| --- | --- | --- |
|  | Positive Cases | Total Cases |
| Breast Adenocarcinoma | 56 | 88 |

TABLE 3-continued
ADENOCARCINOMA DISTRIBUTION OF HB-8986

|  | Positive Cases | Total Cases |
|---|---|---|
| IntraDuctal | 6 | 8 |
| Infiltrating Ductal | 41 | 62 |
| Lobular | 5 | 8 |
| Medullary | 3 | 8 |
| Colloid | 1 | 2 |
| Adenocarcinoma of Stomach | 8 | 20 |
| Adenocarcinoma of Gall Bladder | 1 | 2 |
| Adenocarcinoma of Pancreas | 1 | 1 |
| Adenocarcinoma of Colon | 13 | 39 |
| Adenocarcinoma of Endometrium | 3 | 10 |
| Adenocarcinoma of Ovary |  |  |
| Serous | 1 | 3 |
| Mucinous | 1 | 2 |
| Renal Cell Carcinoma | 0 | 8 |
| Adenocarcinoma of Prostate | 0 | 15 |
| Adenocarcinoma of Thyroid | 6 | 6 |
| Adenocarconoma of Liver | 0 | 5 |

Many tumors with a well differentiated pattern of glandular structures showed strong reactivity; however, areas lacking well defined glands within the same tumors also react positively. In a few cases, the less differentiated area showed strong immunoreactivity while areas of clearly glandular structures showed either weak or no staining. Adenocarcinomas of the endometrium and ovary showed spotty but varying variable but generally weak immuno staining. Adenocarcinomas of the kidney and prostate were consistently negative.

As a group, breast carcinomas of all major types show the most frequent and in some cases the strongest reactivity of the neoplasm study. Epithelial cells in the malignancy studied, showed strong cytoplasmic and/or membrane staining. This pattern was consistently reported in cells of intraductal, infiltrating ductal, lobular, mudullary and colloid carcinomas. The well differentiated and poorly differentiated areas showed similar reactivity.

According to the present invention there is provided: a hybridoma capable of producing an antibody against an antigen found on adenocarcinoma cells and the A549 cell line; a method of producing the hybridoma, and a method of producing the monoclonal antibody.

Although only a single hybridoma producing a single monoclonal antibody against the adenocarcinoma antigen is described, it is contemplated that the present invention encompasses all monoclonal antibodies exhibiting the characteristics described herein. It was determined that the subject antibody belongs to the subclass $IgG_1$, which is one of four subclasses of mjrine IgG. The subclasses of immune globulin G differ from one another in the so-called "fixed" regions. An antibody to a specific antigen will have a so-called "variable" region. A monoclonal antibody exhibiting the characteristic described herein may be of a subclass $IgG_1$, $IgG_{2a}$, $IgG_{2b}$, $IgG_3$ are of classes IgM, IgA, IgE, or IgD. The differences in one of these classes or subclasses will not affect the selectivity of the reaction pattern of the antibody but may affect the further reaction of the antibody with other materials, such as complement. Although the subject antibody is specifically $IgG_1$, it is contemplated that the antibodies having the pattern of the reactivity illustrated herein are included within this subject invention regardless of the immune globulin class or subclass to which they belong.

Further included within the subject invention are methods for preparing the monoclonal antibodies described above employing the hybridoma technique illustrated herein. Although only one example of a hybridoma is given herein, it is contemplated that one skilled in the art could follow the immunization, fusion and selection methods provided herein and obtain other hybridomas capable of producing antibodies having the reactivity characteristics described herein. Within practical means the individual hybridoma produced from the known cell line in spleen cells from a known species of mouse cannot be further identified if set by a reference to the antibody produced by the hybridoma, it is contemplated that all hybridomas producing antibody having the reactivity characteristics described above are included within the subject invention, as are methods of making this antibody employing the hybridoma.

In view of known diagnostic and therapeutic methods, the present invention additionally includes diagnostic and therapeutic compositions comprising a diagnostically effective or therapeutically effective amount of the monoclonal antibody in a diagnostically or pharmaceutically acceptable carrier.

We claim:

1. The hybridoma deposited under ATCC Accession Numer HB 8986.

2. The monoclonal antibody produced by the hybridoma deposited under ATCC Accession Number HB 8986 and clones thereof.

* * * * *